(12) United States Patent
Liang et al.

(10) Patent No.: US 8,232,224 B2
(45) Date of Patent: Jul. 31, 2012

(54) METHODS FOR MAKING CATALYSTS FOR METHACROLEIN OXIDATION

(75) Inventors: Wugeng Liang, Suger Land, TX (US); Scott A. Stevenson, Houston, TX (US); Angie McGuffey, Sugar Land, TX (US)

(73) Assignee: Saudi Basic Industries Corporation (SA)

( * ) Notice: Subject to any disclaimer, the term of this patent is extended or adjusted under 35 U.S.C. 154(b) by 0 days.

(21) Appl. No.: 12/949,532

(22) Filed: Nov. 18, 2010

(65) Prior Publication Data

US 2011/0143931 A1 Jun. 16, 2011

Related U.S. Application Data

(62) Division of application No. 11/189,126, filed on Jul. 25, 2005, now Pat. No. 7,851,397.

(51) Int. Cl.
*B01J 27/00* (2006.01)
*B01J 27/198* (2006.01)
*B01J 27/188* (2006.01)
*B01J 27/19* (2006.01)
*B01J 27/192* (2006.01)

(52) U.S. Cl. ........ 502/208; 502/209; 502/210; 502/211; 502/212

(58) Field of Classification Search .......... 502/208–212; 562/535
See application file for complete search history.

(56) References Cited

U.S. PATENT DOCUMENTS

| | | | | |
|---|---|---|---|---|
| 4,966,990 A | * | 10/1990 | Otake et al. | 560/214 |
| 6,946,422 B2 | * | 9/2005 | Stevenson et al. | 502/311 |
| 7,732,367 B2 | * | 6/2010 | Stevenson et al. | 562/535 |

* cited by examiner

*Primary Examiner* — Patricia L Hailey
(74) *Attorney, Agent, or Firm* — Robert W. Strozier

(57) ABSTRACT

Methods for preparing catalysts for oxidation of unsaturated and/or saturated aldehydes to unsaturated acids is disclosed where the catalyst includes at least molybdenum (Mo), phosphorus (P), vanadium (V), bismuth (Bi), where the bismuth component was dissolved in an organic acid solution prior to adding the bismuth containing solution to a solution of the other components.

19 Claims, No Drawings

METHODS FOR MAKING CATALYSTS FOR METHACROLEIN OXIDATION

RELATED APPLICATIONS

This application is a Divisional Application and claims priority to and the benefit of U.S. patent application Ser. No. 11/189,126 filed Jul. 25, 2005, published as US 2007-0021630 on Jan. 25, 2007.

BACKGROUND OF THE INVENTION

1. Field of the Invention

The present invention relates to a heteropolyacid catalyst including molybdenum (Mo), and phosphorus (P) for use in producing unsaturated acids such as acrylic acid, methacrylic acid or the like in the gas-phase catalytic oxidation of unsaturated aldehydes such as methacrolein, acrolein, or the like or saturated aldehydes such as isobutyraldehyde, where the catalyst components are acidified using an organic acid and method for making and using same.

More particularly, the present invention relates to a heteropolyacid catalyst including molybdenum (Mo) and phosphorus (P) and optionally vanadium (V), bismuth (Bi), and copper (Cu), an optional first component selected from the group consisting of potassium (K), rubidium (Rb), cesium (Cs), thallium (Tl), or mixtures or combinations thereof, and an optional second component selected from the group consisting of antimony (Sb), boron (B), tungsten (W), cerium (Ce), niobium (Nb), indium (In), iron (Fe), chromium (Cr), cobalt (Co), nickel (Ni), manganese (Mn), arsenic (As), silver (Ag), zinc (Zn), lead (Pb), tin (Sn), titanium (Ti), aluminum (Al), silicon (Si), tantalum (Ta), germanium (Ge), gallium (Ga), zirconium (Zr), magnesium (Mg), barium (Ba), lanthanum (La), or mixtures or combinations thereof, used in producing unsaturated acids such as acrylic acid, methacrylic acid or the like by the gas-phase catalytic oxidation of unsaturated aldehydes such as acrolein, methacrolein, or the like or saturated aldehydes such as isobutyraldehyde, where the catalyst components are acidified with an organic acid and when a bismuth component is included as a catalyst component, the bismuth component is dissolved in the organic acid prior to mixing the bismuth component with a solution of the other components, and method for making and using same.

2. Description of the Related Art

Many, if not all, prior art heteropolyacid catalysts for the production of unsaturated acids from unsaturated aldehydes have taught the use of nitric acid or other strong mineral acids in the preparation of the heteropolyacid catalyst, while certain prior art patents have taught a critical nitric acid ($HNO_3$) concentration for the preparation of heteropolyacid catalysts, especially heteropolyacid catalysts including bismuth as one of the catalyst components. U.S. Pat. No. 5,102,846 discloses a catalyst preparation using a critical amount of $HNO_3$ to form a heteropoly acid with improved activity and to dissolve bismuth nitrate when present, while U.S. Pat. No. 5,102,847 discloses a catalyst made by using at least one bismuth compound selected from the group consisting of bismuth nitrate and bismuth oxide as a source of bismuth and using nitric acid of more than 1 mole to not more than 5 moles based on 12 moles of molybdenum atoms for dissolving the bismuth compound(s). U.S. Pat. No. 6,624,326 discloses a process for producing methacrylic acid through vapor phase oxidation or vapor phase oxydehydrogenation of at least one of methacrolein, isobutyl aldehyde and isobutyric acid in the presence of a heteropolyacid catalyst containing a heteropolyacid composed of at least one of molybdophosphoric acid and molybdovanadophosphoric acid or a salt of the heteropolyacid, characterized in that said heteropolyacid catalyst has been prepared by a method comprising preparing an aqueous solution or aqueous dispersion which (1) contains the nitrogen-containing heterocyclic compound, nitrate anions and ammonium ions, (2) the ammonium ion content not exceeding 1.7 moles per mol of the nitrate anion content, and (3) the ammonium ion content not exceeding 10 mols per 12 mols of the molybdenum atom content, by mixing raw materials containing the catalyst-constituting elements with the nitrogen-containing heterocyclic compound in the presence of water, drying and calcining the same.

Because the decomposition of nitrates during catalyst calcination leads to the production of NOx and other hazardous greenhouse gases, replacing the nitric acid used in the preparation of heteropolyacid catalysts would result in a more environmentally benign catalyst preparation process.

Moreover, during the decomposition of nitrates during the calcination process, the reaction heat associated with the decomposition may result in a strong exotherm. If the heat of decomposition cannot be removed or dissipated quickly, this exotherm may result in a temperature rise in the catalyst bed, which sometimes may be higher than the calcination temperature; as a result, the catalyst structure can be damaged. The exotherm may be more significant in large-scale preparation (commercial scale) of the catalysts. Replacing nitric acid with an organic acid will significantly reduce the exotherm, because organic acid decomposition occurs at a lower temperature.

Thus, there is still a need in the art for improved catalysts for the gas phase oxidation of aldehydes to unsaturated acids, such as acrylic acid or methacrylic acid, where the catalyst is prepared from a solution acidified with an organic acid instead of nitric acid.

DEFINITIONS AND ABBREVIATIONS

The term IBA means isobutanal sometimes also referred to as isobutyraldehyde.

The term MAC means methacrolein.

The term MAA means methacryclic acid.

The term T means temperature.

The term P means pressure.

The term HC means hydrocarbon.

The term aldehyde feedstock means a stream including mixtures of isobutanal and methacrolein.

The term GC means gas chromatography.

The term FID means flame ionization detector of a GC.

The term h or hr or hrs means hours.

The term g means grams.

The term mL means milliliter.

the term min or min. means minutes.

The term wt % or wt. % means weight percent.

The term vol % or vol. % means volume percent.

The term DI water means deionized water.

The term pore volume distribution means a desired concentration of small pores, medium pores and large pores.

The term small pores means pores having a diameter D less than about 100 Å, i.e., D<100 Å.

The term medium pores means pores having a diameter D greater than or equal to about 100 Å and less than about 1000 Å, i.e., 100 Å≦D<1000 Å.

The term large pore volume means pores having a diameter D greater than or equal to about 1000 Å, i.e., D≧1000 Å.

SUMMARY OF THE INVENTION

General Catalyst Compositions

The present invention provides a novel, highly active and highly selective, heteropolyacid catalyst including at least molybdenum (Mo) and phosphorus (P), adapted to gas-phase oxidize unsaturated and/or saturated aldehydes to unsaturated acids, where the catalyst components are acidified with an organic acid. The use of an organic acid to acidify the pre-catalyst solution, mixture or slurry generally produces catalyst with higher amount of medium pores, but an optional amount of an ammonium-containing compound can also be added to the catalyst to increase the amount of medium pores formed in the catalyst.

The present invention provides a novel, highly active and highly selective, heteropolyacid catalyst including at least molybdenum (Mo) and phosphorus (P), adapted to gas-phase oxidize unsaturated and/or saturated aldehydes to unsaturated acids, where the catalyst is prepared using an organic acid to acidify the catalyst precursor solution. The use of an organic acid to acidify the pre-catalyst solution, mixture or slurry generally produces catalyst with higher amount of medium pores, but an optional amount of an ammonium-containing compound can also be added to the catalyst to increase the amount of medium pores formed in the catalyst. Preferably, a majority (>50%) of the pores in the catalyst are medium pores.

The present invention provides a novel, highly active and highly selective, heteropolyacid catalyst including at least molybdenum (Mo), phosphorus (P) and vanadium (V), adapted to gas-phase oxidize unsaturated and/or saturated aldehydes to unsaturated acids, where the catalyst components are acidified with an organic acid. The use of an organic acid to acidify the pre-catalyst solution, mixture or slurry generally produces catalyst with higher amount of medium pores, but an optional amount of an ammonium-containing compound can also be added to the catalyst to increase the amount of medium pores formed in the catalyst. Preferably the resulting catalyst has a pore size distribution comprising at least 57% medium pores.

The present invention provides a novel, highly active and highly selective, heteropolyacid catalyst including at least molybdenum (Mo), phosphorus (P), vanadium (V) and bismuth (Bi), adapted to gas-phase oxidize unsaturated and/or saturated aldehydes to unsaturated acids, where the catalyst components are acidified with an organic acid. The use of an organic acid to acidify the pre-catalyst solution, mixture or slurry generally produces catalyst with higher amount of medium pores, but an optional amount of an ammonium-containing compound can also be added to the catalyst to increase the amount of medium pores formed in the catalyst. Preferably the resulting catalyst has a pore size distribution comprising at least 57% medium pores.

The present invention provides a novel, highly active and highly selective, heteropolyacid catalyst including at least molybdenum (Mo), phosphorus (P), vanadium (V), bismuth (Bi), and a first component selected from the group consisting of potassium (K), rubidium (Rb), cesium (Cs), thallium (Tl), or mixtures or combinations thereof, adapted to gas-phase oxidize unsaturated and/or saturated aldehydes to unsaturated acids, where the catalyst components are acidified with an organic acid. The use of an organic acid to acidify the pre-catalyst solution, mixture or slurry generally produces catalyst with higher amount of medium pores, but an optional amount of an ammonium-containing compound can also be added to the catalyst to increase the amount of medium pores formed in the catalyst. Preferably the resulting catalyst has a pore size distribution comprising at least 57% medium pores.

The present invention provides a novel, highly active and highly selective, heteropolyacid catalyst including at least molybdenum (Mo), phosphorus (P), vanadium (V), bismuth (Bi), and a first component selected from the group consisting of potassium (K), rubidium (Rb), cesium (Cs), thallium (Tl), or mixtures or combinations thereof, adapted to gas-phase oxidize unsaturated and/or saturated aldehydes to unsaturated acids, where the bismuth component is dissolved in an organic acid solution prior to mixing the bismuth component with a solution of other components and where the unsaturated aldehydes are selected from the group consisting of methacrolein, acrolein, similar unsaturated aldehydes and mixtures or combinations thereof or saturated aldehydes including isobutyraldehyde and where the unsaturated acids are selected from the group consisting of acrylic acid, methacrylic acid, similar unsaturated acids, and mixtures or combinations thereof. The use of an organic acid to acidify the pre-catalyst solution, mixture or slurry generally produces catalyst with higher amount of medium pores, but an optional amount of an ammonium-containing compound can also be added to the catalyst to increase the amount of medium pores formed in the catalyst. Preferably, a majority (>50%) of the pores in the catalyst are medium pores.

The present invention also provides a heteropolyacid catalyst including molybdenum (Mo), phosphorus (P), vanadium (V), bismuth (Bi), and optionally, copper (Cu), a first component selected from the group consisting of potassium (K), rubidium (Rb), cesium (Cs), thallium (Tl), or mixtures or combinations thereof, and an optional second component selected from the group consisting of antimony (Sb), boron (B), tungsten (W), cerium (Ce), niobium (Nb), indium (In), iron (Fe), chromium (Cr), cobalt (Co), nickel (Ni), manganese (Mn), arsenic (As), silver (Ag), zinc (Zn), lead (Pb), tin (Sn), titanium (Ti), aluminum (Al), silicon (Si), tantalum (Ta), germanium (Ge), gallium (Ga), zirconium (Zr), magnesium (Mg), barium (Ba), lanthanum (La), or mixtures or combinations thereof, used for gas-phase catalytic oxidation of unsaturated aldehydes such as methacrolein, acrolein, or the like or saturated aldehydes such as isobutyraldehyde to unsaturated acids such as acrylic acid, methacrylic acid or the like, where the bismuth component is dissolved in an organic acid solution prior to mixing the bismuth component with a solution of other components and where the unsaturated aldehydes are selected from the group consisting of acrolein, methacrolein, similar unsaturated aldehydes or isobutyraldehyde and mixtures or combinations thereof and where the unsaturated acids are selected from the group consisting of acrylic acid, methacrylic acid, similar unsaturated acids, and mixtures or combinations thereof. The use of an organic acid to acidify the pre-catalyst solution, mixture or slurry generally produces a catalyst with a higher amount of medium pores, but an optional amount of an ammonium-containing compound can also be added to the catalyst to increase the amount of medium pores formed in the catalyst. Preferably, the amount of the ammonium-containing component added to the catalyst preparation is sufficient to produce a catalyst of this invention having a pore size distribution comprising at least 57% medium pores.

The present invention also provides a novel, highly active and highly selective, heteropolyacid catalyst for converting unsaturated and/or saturated aldehydes to unsaturated acids of the general formula:

$$Mo_{12}P_aV_bCu_cBi_dMI_eMII_fO_g \qquad (I)$$

where:
- MI is selected from the group consisting of potassium (K), rubidium (Rb), cesium (Cs), thallium (Tl), and mixtures or combinations thereof,
- MII is selected from the group consisting of antimony (Sb), boron (B), tungsten (W), cerium (Ce), niobium (Nb), indium (In), iron (Fe), chromium (Cr), cobalt (Co), nickel (Ni), manganese (Mn), arsenic (As), silver (Ag), zinc (Zn), lead (Pb), tin (Sn), titanium (Ti), aluminum (Al), silicon (Si), tantalum (Ta), germanium (Ge), gallium (Ga), zirconium (Zr), magnesium (Mg), barium (Ba), lanthanum (La), and mixtures or combinations thereof,
- a is a number having a value between about 0.5 and about 3.5,
- b is a number having a value between 0.00 and about 5.0,
- c is a number having a value between 0.00 and about 1.5,
- d is a number having a value between 0.00 and about 2.0,
- e is a number having a value between 0.00 and about 2.5,
- f is a number having a value between 0.00 and about 5.0,
- g is a number having a value representing a sufficient number of oxygen atoms to balance the oxidation state of the catalyst of formula (I),
- if present, the bismuth component is dissolved in an organic acid solution prior to mixing the bismuth component with a solution of the other components.

The present invention also provides a novel, highly active and highly selective, heteropolyacid catalyst for converting unsaturated and/or saturated aldehydes to unsaturated acids of the general formula:

$$Mo_{12}P_aV_bCu_cBi_dMI_eMII_fO_g \quad (II)$$

where:
- MI is selected from the group consisting of potassium (K), rubidium (Rb), cesium (Cs), thallium (Tl), and mixtures or combinations thereof,
- MII is selected from the group consisting of antimony (Sb), boron (B), tungsten (W), cerium (Ce), niobium (Nb), indium (In), iron (Fe), chromium (Cr), cobalt (Co), nickel (Ni), manganese (Mn), arsenic (As), silver (Ag), zinc (Zn), lead (Pb), tin (Sn), titanium (Ti), aluminum (Al), silicon (Si), tantalum (Ta), germanium (Ge), gallium (Ga), zirconium (Zr), magnesium (Mg), barium (Ba), lanthanum (La), and mixtures or combinations thereof,
- a is a number having a value between about 0.5 and about 3.5,
- b is a number having a value between about 0.01 and about 5.0,
- c is a number having a value between 0.00 and about 1.5,
- d is a number having a value between 0.00 and about 2.0,
- e is a number having a value between 0.00 and about 2.5,
- f is a number having a value between 0.00 and about 5.0,
- g is a number having a value representing a sufficient number of oxygen atoms to balance the oxidation state of the catalyst of formula (II), and
- if present, the bismuth component is dissolved in an organic acid solution prior to mixing the bismuth component with a solution of the other components.

The present invention also provides a novel, highly active and highly selective, heteropolyacid catalyst for converting unsaturated and/or saturated aldehydes to unsaturated acids of the general formula:

$$Mo_{12}P_aV_bCu_cBi_dMI_eMII_fO_g \quad (III)$$

where:
- MI is selected from the group consisting of potassium (K), rubidium (Rb), cesium (Cs), thallium (Tl), and mixtures or combinations thereof,
- MII is selected from the group consisting of antimony (Sb), boron (B), tungsten (W), cerium (Ce), niobium (Nb), indium (In), iron (Fe), chromium (Cr), cobalt (Co), nickel (Ni), manganese (Mn), arsenic (As), silver (Ag), zinc (Zn), lead (Pb), tin (Sn), titanium (Ti), aluminum (Al), silicon (Si), tantalum (Ta), germanium (Ge), gallium (Ga), zirconium (Zr), magnesium (Mg), barium (Ba), lanthanum (La), and mixtures or combinations thereof,
- a is a number having a value between about 0.5 and about 3.5,
- b is a number having a value between 0.00 and about 5.0,
- c is a number having a value between 0.00 and about 1.5,
- d is a number having a value between about 0.01 and about 2.0,
- e is a number having a value between 0.00 and about 2.5,
- f is a number having a value between 0.00 and about 5.0,
- g is a number having a value representing a sufficient number of oxygen atoms to balance the oxidation state of the catalyst of formula (III), and
- the bismuth component is dissolved in an organic acid solution prior to mixing the bismuth component with a solution of the other components.

The present invention also provides a novel, highly active and highly selective, heteropolyacid catalyst for converting unsaturated and/or saturated aldehydes to unsaturated acids of the general formula:

$$Mo_{12}P_aV_bCu_cBi_dMI_eMII_fO_g \quad (IV)$$

where:
- MI is selected from the group consisting of potassium (K), rubidium (Rb), cesium (Cs), thallium (Tl), and mixtures or combinations thereof,
- MII is selected from the group consisting of antimony (Sb), boron (B), tungsten (W), cerium (Ce), niobium (Nb), indium (In), iron (Fe), chromium (Cr), cobalt (Co), nickel (Ni), manganese (Mn), arsenic (As), silver (Ag), zinc (Zn), lead (Pb), tin (Sn), titanium (Ti), aluminum (Al), silicon (Si), tantalum (Ta), germanium (Ge), gallium (Ga), zirconium (Zr), magnesium (Mg), barium (Ba), lanthanum (La), and mixtures or combinations thereof,
- a is a number having a value between about 0.5 and about 3.5,
- b is a number having a value between about 0.01 and about 5.0,
- c is a number having a value between 0.00 and about 1.5,
- d is a number having a value between about 0.01 and about 2.0,
- e is a number having a value between 0.00 and about 2.5,
- f is a number having a value between 0.00 and about 5.0,
- g is a number having a value representing a sufficient number of oxygen atoms to balance the oxidation state of the catalyst of formula (IV), and
- the bismuth component is dissolved in an organic acid solution prior to mixing the bismuth component with a solution of the other components.

The present invention also provides a novel, highly active and highly selective, heteropolyacid catalyst for converting unsaturated and/or saturated aldehydes to unsaturated acids of the general formula:

$$Mo_{12}P_aV_bCu_cBi_dMI_eMII_fO_g \quad (V)$$

where:
- MI is selected from the group consisting of potassium (K), rubidium (Rb), cesium (Cs), thallium (Tl), and mixtures or combinations thereof,
- MII is selected from the group consisting of antimony (Sb), boron (B), tungsten (W), cerium (Ce), niobium (Nb), indium (In), iron (Fe), chromium (Cr), cobalt (Co), nickel (Ni), manganese (Mn), arsenic (As), silver (Ag), zinc (Zn), lead (Pb), tin (Sn), titanium (Ti), aluminum (Al), silicon (Si), tantalum (Ta), germanium (Ge), gallium (Ga), zirconium (Zr), magnesium (Mg), barium (Ba), lanthanum (La), and mixtures or combinations thereof,
- a is a number having a value between about 0.5 and about 3.5,
- b is a number having a value between about 0.01 and about 5.0,
- c is a number having a value between about 0.01 and about 1.5,
- d is a number having a value between about 0.01 and about 2.0,
- e is a number having a value between 0.00 and about 2.5,
- f is a number having a value between 0.00 and about 5.0,
- g is a number having a value representing a sufficient number of oxygen atoms to balance the oxidation state of the catalyst of formula (V), and
- the bismuth component is dissolved in an organic acid solution prior to mixing the bismuth component with a solution of the other components.

The present invention also provides a novel, highly active and highly selective, heteropolyacid catalyst for converting unsaturated and/or saturated aldehydes to unsaturated acids of the general formula:

$$Mo_{12}P_aV_bCu_cBi_dMI_eMII_fO_g \quad \text{(VI)}$$

where:
- MI is selected from the group consisting of potassium (K), rubidium (Rb), cesium (Cs), thallium (Tl), and mixtures or combinations thereof,
- MII is selected from the group consisting of antimony (Sb), boron (B), tungsten (W), cerium (Ce), niobium (Nb), indium (In), iron (Fe), chromium (Cr), cobalt (Co), nickel (Ni), manganese (Mn), arsenic (As), silver (Ag), zinc (Zn), lead (Pb), tin (Sn), titanium (Ti), aluminum (Al), silicon (Si), tantalum (Ta), germanium (Ge), gallium (Ga), zirconium (Zr), magnesium (Mg), barium (Ba), lanthanum (La), and mixtures or combinations thereof,
- a is a number having a value between about 0.5 and about 3.5,
- b is a number having a value between about 0.01 and about 5.0,
- c is a number having a value between about 0.01 and about 1.5,
- d is a number having a value between about 0.01 and about 2.0,
- e is a number having a value between about 0.01 and about 2.5,
- f is a number having a value between 0.00 and about 5.0,
- g is a number having a value representing a sufficient number of oxygen atoms to balance the oxidation state of the catalyst of formula (VI), and
- the bismuth component is dissolved in an organic acid solution prior to mixing the bismuth component with a solution of the other components.

The present invention also provides a novel, highly active and highly selective, heteropolyacid catalyst for converting unsaturated and/or saturated aldehydes to unsaturated acids of the general formula:

$$Mo_{12}P_aV_bCu_cBi_dMI_eMII_fO_g \quad \text{(VII)}$$

where:
- MI is selected from the group consisting of potassium (K), rubidium (Rb), cesium (Cs), thallium (Tl), and mixtures or combinations thereof,
- MII is selected from the group consisting of antimony (Sb), boron (B), tungsten (W), cerium (Ce), niobium (Nb), indium (In), iron (Fe), chromium (Cr), cobalt (Co), nickel (Ni), manganese (Mn), arsenic (As), silver (Ag), zinc (Zn), lead (Pb), tin (Sn), titanium (Ti), aluminum (Al), silicon (Si), tantalum (Ta), germanium (Ge), gallium (Ga), zirconium (Zr), magnesium (Mg), barium (Ba), lanthanum (La), and mixtures or combinations thereof,
- a is a number having a value between about 0.5 and about 3.5,
- b is a number having a value between about 0.01 and about 5.0,
- c is a number having a value between about 0.01 and about 1.5,
- d is a number having a value between about 0.01 and about 2.0,
- e is a number having a value between about 0.01 and about 2.5,
- f is a number having a value between about 0.01 and about 5.0,
- g is a number having a value representing a sufficient number of oxygen atoms to balance the oxidation state of the catalyst of formula (VII), and
- the bismuth component is dissolved in an organic acid solution prior to mixing the bismuth component with a solution of the other components.

The present invention also provides a novel, highly active and highly selective, heteropolyacid catalyst for converting unsaturated and/or saturated aldehydes to unsaturated acids of the general formula:

$$Mo_{12}P_aV_bCu_cBi_dMI_eMII_fO_g \quad \text{(VIII)}$$

where:
- MI is selected from the group consisting of potassium (K), rubidium (Rb), cesium (Cs), thallium (Tl), and mixtures or combinations thereof,
- MII is selected from the group consisting of antimony (Sb), boron (B), tungsten (W), cerium (Ce), niobium (Nb), indium (In), iron (Fe), chromium (Cr), cobalt (Co), nickel (Ni), manganese (Mn), arsenic (As), silver (Ag), zinc (Zn), lead (Pb), tin (Sn), titanium (Ti), aluminum (Al), silicon (Si), tantalum (Ta), germanium (Ge), gallium (Ga), zirconium (Zr), magnesium (Mg), barium (Ba), lanthanum (La), and mixtures or combinations thereof,
- a is a number having a value between about 0.5 and about 3.5,
- b is a number having a value between about 0.1 and about 5.0,
- c is a number having a value between about 0.05 and about 1.5,
- d is a number having a value between about 0.1 and about 2.0,
- e is a number having a value between about 0.2 and about 2.5, f is a number having a value between about 0.1 and about 5.0, g is a number having a value representing a sufficient number of oxygen atoms to balance the oxidation state of the catalyst of formula (VIII), the bismuth component is dissolved in an organic acid solution prior to mixing the bismuth component with a solution of the other components.

The present invention also provides a novel, highly active and highly selective, heteropolyacid catalyst for converting unsaturated and/or saturated aldehydes to unsaturated acids of the general formula:

$$Mo_{12}P_aV_bCu_cBi_dMI_eMII_fO_g \qquad (IX)$$

where:

MI is selected from the group consisting of potassium (K), rubidium (Rb), cesium (Cs), thallium (Tl), and mixtures or combinations thereof, at least two elements MII selected from the group consisting of antimony (Sb), boron (B), tungsten (W), cerium (Ce), niobium (Nb), indium (In), iron (Fe), chromium (Cr), cobalt (Co), nickel (Ni), manganese (Mn), arsenic (As), silver (Ag), zinc (Zn), lead (Pb), tin (Sn), titanium (Ti), aluminum (Al), silicon (Si), tantalum (Ta), germanium (Ge), gallium (Ga), zirconium (Zr), magnesium (Mg), barium (Ba), lanthanum (La), and mixtures or combinations thereof, a is a number having a value between about 1.0 and about 2.5, b is a number having a value between about 0.1 and about 2.5, c is a number having a value between about 0.05 and about 0.5, d is a number having a value between about 0.1 and about 1.0, e is a number having a value between about 0.2 and about 2.0, f is a number having a value between about 0.1 and about 2.0, g is a number having a value representing a sufficient number of oxygen atoms to balance the oxidation state of the catalyst of formula (IX), the bismuth component is dissolved in an organic acid solution prior to mixing the bismuth component with a solution of the other components.

Methods for Preparing Catalysts

The present invention provides a method for preparing a novel, highly active and highly selective, heteropolyacid catalyst for converting unsaturated and/or saturated aldehydes to unsaturated acids. The references to moles used in describing the preparation of the catalysts of this invention mean relative molar amounts, e.g., if 1 mole of catalyst is being prepared, the catalyst will have moles of components such that the molar ratio of molybdenum to the other components in the catalyst is 12. As another example, to make a catalyst having the formula $Mo_{12}P_aV_bCu_cBi_dMI_eMII_fO_g$, the number of moles of components used during catalyst preparation will be in a molar ratio of 12:a:b:c:d:e:f:g.

The method includes the step of forming a mixture of 12 moles of molybdenum (1 mole of $Mo_{12}$), a moles of phosphorus (P), b moles of vanadium (V), c moles of copper (Cu), d moles of bismuth (Bi), e moles of a first component selected from the group consisting of potassium (K), rubidium (Rb), cesium (Cs), thallium (Tl), or mixtures or combinations thereof and f moles of a second component selected from the group consisting of antimony (Sb), boron (B), tungsten (W), cerium (Ce), niobium (Nb), indium (In), iron (Fe), chromium (Cr), cobalt (Co), nickel (Ni), manganese (Mn), arsenic (As), silver (Ag), zinc (Zn), lead (Pb), tin (Sn), titanium (Ti), aluminum (Al), silicon (Si), tantalum (Ta), germanium (Ge), gallium (Ga), zirconium (Zr), magnesium (Mg), barium (Ba), lanthanum (La), and mixtures or combinations thereof, where the mixture slurry is acidified with an organic acid and where a is a number having a value between about 0.5 and about 3.5, b is a number having a value between 0.0 and about 5.0, c is a number having a value between 0.0 and about 1.5, d is a number having a value between 0.0 and about 2.0, e is a number having a value between 0.0 and about 2.5, f is a number having a value between 0.0 and about 5.0, where all mole values are relative and g moles of oxygen atoms needed to balance the oxidation state of the catalyst. As shown in the preferred catalysts of this invention as set forth in Formulas (I-VI), the other catalyst components having relative mole amounts b, c, d, e, and f can be added to the catalyst preparation in any order with starting amounts of: 0.01 for b, 0.01 for c, 0.01 for d, 0.01 for e, and 0.01 for f.

When bismuth is used, then the bismuth is first dissolved in the organic acid and this solution is then added to a solution of the other components. Preferably, if the first component is cesium, then the cesium is added to the solution of the other components. The pre-catalyst, which can be a solution, slurry, dispersion or suspension is then evaporated to form a dried catalytic material, which is then calcined to form a catalyst of this invention. The use of an organic acid to acidify the pre-catalyst solution, mixture or slurry generally produces catalyst with higher amount of medium pores, but an optional amount of an ammonium-containing compound can also be added to the catalyst to increase the amount of medium pores formed in the catalyst. Preferably, the amount of an ammonium-containing component is added to the catalyst preparation to produce a pore size distribution comprising at least 50% medium pores, preferably, at least 57% medium pores.

The present invention also provides a method for preparing preferred novel, highly active and highly selective, heteropolyacid catalysts of Formula (VII) for converting unsaturated and/or saturated aldehydes to unsaturated acids including the steps of forming a first solution including 12 moles of molybdenum (1 mole of $Mo_{12}$), a moles of phosphorus (P), b moles of vanadium (V), c moles of copper (Cu), optionally d moles of bismuth (Bi), e moles of a first component selected from the group consisting of potassium (K), rubidium (Rb), cesium (Cs), thallium (Tl), or mixtures or combinations thereof and f moles of a second component selected from the group consisting of antimony (Sb), boron (B), tungsten (W), cerium (Ce), niobium (Nb), indium (In), iron (Fe), chromium (Cr), cobalt (Co), nickel (Ni), manganese (Mn), arsenic (As), silver (Ag), zinc (Zn), lead (Pb), tin (Sn), titanium (Ti), aluminum (Al), silicon (Si), tantalum (Ta), germanium (Ge), gallium (Ga), zirconium (Zr), magnesium (Mg), barium (Ba), lanthanum (La), and mixtures or combinations thereof, where the slurry is acidified with an organic acid and where a is a number having a value between about 0.5 and about 3.5, b is a number having a value between about 0.01 and about 5.0, c is a number having a value between 0.01 and about 1.5, d is a number having a value between 0.01 and about 2.0, e is a number having a value between 0.02 and about 2.5, and f is a number having a value between 0.01 and about 5.0.

The present invention provides a method for preparing a novel, highly active and highly selective, heteropolyacid catalyst for converting unsaturated and/or saturated aldehydes to unsaturated acids including the steps of forming a first solution including 12 moles of molybdenum (1 mole of $Mo_{12}$), a moles of phosphorus (P), b moles of vanadium (V), c moles of copper (Cu), all or some of e moles of a first component selected from the group consisting of potassium (K), rubidium (Rb), cesium (Cs), thallium (Tl), or mixtures or combinations thereof and all or some of f moles of a second component selected from the group consisting of antimony (Sb), boron (B), tungsten (W), cerium (Ce), niobium (Nb), indium (In), iron (Fe), chromium (Cr), cobalt (Co), nickel (Ni), manganese (Mn), arsenic (As), silver (Ag), zinc (Zn), lead (Pb), tin (Sn), titanium (Ti), aluminum (Al), silicon (Si), tantalum (Ta), germanium (Ge), gallium (Ga), zirconium (Zr), magnesium (Mg), barium (Ba), lanthanum (La), and mixtures or combinations thereof, where a is a number having a value between about 0.5 and about 3.5, b is a number having a value between about 0.01 and about 5.0, c is a number having a value between 0.01 and about 1.5, d is a number having a value between about 0.01 and about 2.0, e is a number having a value between about 0.2 and about 2.5 and f is a number having a value between 0.01 and about 5.0, where the first solution is preferably substantially free of precipitates. The term substantially free of precipitates means that the amount of precipitate present in the solution is less than 5 wt. %, preferably less than 2.5 wt. %, particularly less than 1 wt. % and especially less than 0.5 wt. %, with the ultimate goal being completely solid-free or precipitate-free.

Prior to, simultaneous with or after the formation of the first solution, a bismuth solution including d moles of a bismuth (Bi) component and a sufficient amount of an organic acid to completely dissolve the bismuth component, optionally a remainder of the e moles of the first component and optionally some or all of a remainder of the f moles of the second component is formed, where d is a number having a value between about 0.01 and about 2.0 and the bismuth solution is substantially free of precipitates. The bismuth solution is then added to the first solution to form a slurry. The slurry is then evaporated to form a dried catalytic material, which is then calcined to form a catalyst of this invention.

Alternatively, the slurry is heated to about 95° C. prior to drying and some or all of the remainder of the f moles of second component are added to the heated slurry, where generally the second components added to the heated slurry are second components that require a higher temperature for proper incorporation into the catalyst. The resulting composition is then evaporated to form a dried catalytic material, which is then calcined to form a catalyst of this invention. It should be recognized that many of the components can be added to the first solution, the bismuth solution, the slurry or the catalyst before calcining, depending on the specific catalyst being prepared.

The above method can also be used to prepare preferred catalysts of Formula (VIII) where a is a number having a value between about 0.5 and about 3.5, b is a number having a value between about 0.1 and about 5.0, c is a number having a value between about 0.05 and about 1.5, d is a number having a value between about 0.1 and about 2.0, e is a number having a value between about 0.2 and about 2.5, f is a number having a value between about 0.1 and about 5.0, and g is a number having a value representing a sufficient number of oxygen atoms to balance the oxidation state of the catalyst.

The above method can also be used to prepare preferred catalysts of Formula (IX) where a is a number having a value between about 1.0 and about 2.5, b is a number having a value between about 0.1 and about 2.5, c is a number having a value between about 0.05 and about 0.5, d is a number having a value between about 0.1 and about 1.0, e is a number having a value between about 0.2 and about 2.0, f is a number having a value between about 0.1 and about 2.0, and g moles of oxygen atoms needed to balance the oxidation state of the catalyst.

Methods for Producing Unsaturated Acids

The present invention also provides a method for preparing unsaturated acids including the step of contacting an unsaturated and/or saturated aldehyde with a catalyst of this invention to form a corresponding unsaturated acid, where the method is ideally suited for the production of acrylic acid from acrolein or methacrylic acid from methacrolein or both.

The present invention provides a method for preparing unsaturated acids including the step of contacting an appropriate alkene with a mixed metal oxide catalyst to form a corresponding unsaturated and/or saturated aldehyde and subsequently contacting the unsaturated and/or saturated aldehyde with a catalyst of this invention to form a corresponding unsaturated acid, where the method is ideally suited for the production of acrylic acid and/or methacrylic acid.

DETAILED DESCRIPTION OF THE INVENTION

The inventors have found that a novel, highly active and highly selective, heteropolyacid catalyst of the general formula:

$$Mo_{12}P_aV_bCu_cBi_dMI_eMII_fO_g \qquad (I)$$

where:

MI is selected from the group consisting of potassium (K), rubidium (Rb), cesium (Cs), thallium (Tl), or mixtures or combinations thereof, MII is selected from the group consisting of antimony (Sb), boron (B), tungsten (W), cerium (Ce), niobium (Nb), indium (In), iron (Fe), chromium (Cr), cobalt (Co), nickel (Ni), manganese (Mn), arsenic (As), silver (Ag), zinc (Zn), lead (Pb), tin (Sn), titanium (Ti), aluminum (Al), silicon (Si), tantalum (Ta), germanium (Ge), gallium (Ga), zirconium (Zr), magnesium (Mg), barium (Ba), lanthanum (La), or mixtures or combinations thereof, a is a number having a value between about 0.5 and about 3.5, b is a number having a value between 0.00 and about 5.0, c is a number having a value between 0.00 and about 1.5, d is a number having a value between 0.00 and about 2.0, e is a number having a value between 0.00 and about 2.5, f is a number having a value between 0.00 and about 5.0, g is a number having a value representing a sufficient number of oxygen atoms to balance the oxidation state of the catalyst of formula (I), the catalyst is prepared using an organic acid and if present, the bismuth component is dissolved in a solution including a sufficient concentration of the organic acid to completely dissolve the bismuth component prior to adding the bismuth component to a solution of some or all of the other ingredients, and the catalysts are uniquely designed for the oxidation of unsaturated and/or saturated aldehydes into unsaturated acids, especially, for the oxidation of conjugated unsaturated aldehydes into unsaturated acids.

The inventors have found that the catalysts of Formula (I) can be prepared by a method where the bismuth component is dissolved in a solution including a sufficient amount of an organic acid to substantially dissolve the bismuth component prior to its addition to a solution containing the other components. The catalysts preferably have at least 57% medium pores, which are formed during a controlled calcination process. Although the catalysts of this invention are preferably prepared using water as the solvent, i.e., the liquid phase is an aqueous liquid phase, the catalysts of this invention can be made using a mixed aqueous/organic liquid phase, a mixed aqueous/non-aqueous liquid phase, non-aqueous liquid phase or organic liquid phase. The term organic means a carbon-containing, while the term non-aqueous means a non-aqueous solvent that does not contain carbon.

The present invention broadly relates a novel, highly active and highly selective, heteropolyacid catalyst including at least molybdenum (Mo), phosphorus (P), optionally vanadium (V), optionally bismuth (Bi), and optionally a first component selected from the group consisting of potassium (K), rubidium (Rb), cesium (Cs), thallium (Tl), or mixtures or combinations thereof, adapted to gas-phase oxidize unsaturated aldehydes prepared with an organic acid, especially conjugated unsaturated and/or saturated aldehydes, to unsaturated acids. The catalysts are especially well suited for oxidatively converting unsaturated and/or saturated aldehydes selected from the group consisting of acrolein, methacrolein, similar unsaturated and/or saturated aldehydes and mixtures or combinations thereof to unsaturated acids selected from the group consisting of acrylic acid, methacrylic acid, similar unsaturated acids, and mixtures or combinations thereof. Preferably, the present invention relates to a heteropolyacid catalyst including molybdenum (Mo), phosphorus (P), optionally vanadium (V), optionally bismuth (Bi), optionally, copper (Cu), optionally a first component selected from the group consisting of potassium (K), rubidium (Rb), cesium (Cs), thallium (Tl), or mixtures or combinations thereof, and optionally a second component selected from the group consisting of antimony (Sb), boron (B), tungsten (W), cerium (Ce), niobium (Nb), indium (In), iron (Fe), chromium (Cr), cobalt (Co), nickel (Ni), manganese (Mn), arsenic (As), silver (Ag), zinc (Zn), lead (Pb), tin (Sn), titanium (Ti), aluminum (Al), silicon (Si), tantalum (Ta), germanium (Ge), gallium (Ga), zirconium (Zr), magnesium (Mg), barium (Ba), lanthanum (La), or mixtures or combinations thereof prepared using an organic acid, used for gas-phase catalytic oxidation of unsaturated aldehydes such as methacrolein, acrolein, or the like or unsaturated aldehydes such as isobutyraldehyde to unsaturated acids such as acrylic acid, methacrylic acid or the like. Particularly, the present invention relates to a novel, highly active and highly selective, heteropolyacid catalyst for converting unsaturated and/or saturated aldehydes to unsaturated acids of the general formula:

$$Mo_{12}P_aV_bCu_cBi_dMI_eMII_fO_g \qquad (I)$$

where:
MI is selected from the group consisting of potassium (K), rubidium (Rb), cesium (Cs), thallium (Tl), and mixtures or combinations thereof,
MII is selected from the group consisting of antimony (Sb), boron (B), tungsten (W), cerium (Ce), niobium (Nb), indium (In), iron (Fe), chromium (Cr), cobalt (Co), nickel (Ni), manganese (Mn), arsenic (As), silver (Ag), zinc (Zn), lead (Pb), tin (Sn), titanium (Ti), aluminum (Al), silicon (Si), tantalum (Ta), germanium (Ge), gallium (Ga), zirconium (Zr), magnesium (Mg), barium (Ba), lanthanum (La), and mixtures or combinations thereof,
a is a number having a value between about 0.5 and about 3.5,
b is a number having a value between 0.00 and about 5.0,
c is a number having a value between 0.00 and about 1.5,
d is a number having a value between 0.00 and about 2.0,
e is a number having a value between 0.00 and about 2.5,
f is a number having a value between 0.0 and about 5.0,
g is a number having a value representing a sufficient number of oxygen atoms to balance the oxidation state of the catalyst of formula (I), and prepared using an organic acid and if present, the bismuth component is dissolved in a solution including a sufficient amount of the organic acid to substantially dissolve the bismuth component prior to its addition to a solution containing the other components.

Suitable compounds used for preparation of the catalysts of this invention include, without limitation, metal nitrates, metal carbonates, metal ammonium salts, metal halides, metal oxides, or mixtures or combinations thereof. For example, suitable molybdenum components include, without limitation, ammonium paramolybdate, molybdenum trioxide, molybdenum chloride, etc. or mixtures or combinations thereof. The preferred molybdenum component is ammonium paramolybdate. Suitable vanadium components include, without limitation, ammonium metavanadate, vanadium pentoxide, vanadium chloride, etc. or mixtures or combinations thereof. The preferred vanadium component is ammonium metavanadate. Suitable phosphorus components include, without limitation, phosphoric acid, ammonium phosphate, etc. or mixtures or combinations thereof. The preferred phosphorus component is phosphoric acid. Suitable copper components include, without limitation, copper nitrate, copper chloride, etc. or mixtures or combinations thereof. The preferred copper component is copper nitrate. Suitable bismuth components include, without limitation, bismuth nitrate, bismuth oxide, bismuth acetate, bismuth chloride, etc. or mixtures or combinations thereof. The preferred bismuth component is bismuth nitrate. Suitable MI components include, without limitation, MI nitrates, MI oxides, MI chlorides, etc. or mixtures or combinations thereof. The preferred MI components are MI nitrates and MI oxides or mixtures or combinations thereof. Suitable MII components include, without limitation, MII nitrates, MII oxides, MII chlorides, etc. or mixtures or combinations thereof. The preferred MII components are MII nitrates and MII oxides or mixtures or combinations thereof.

Suitable organic acids for use in the preparation of the catalyst of this invention include, without limitation, any organic acid such as: (1) monocarboxylic acids that are capable of acidifying the preparation to a desired pH value, with or without the addition of a co-acidifying agent such as nitric acid, having between 1 and about 24 carbon atoms, preferably between 1 and about 12 carbon atoms, and particularly between 1 and about 6 carbon atoms, hydroxylated analogs thereof, or other substituted analogs thereof, provided that the substituent is substantially removed during drying, soaking and/or calcining and causes no adverse effects to the final catalyst; and (2) polycarboxylic acids having between 2 and about 24 carbon atoms, preferably between 2 and about 12 carbon atoms, and particularly between 2 and about 6 carbon atoms, hydroxylated analogs thereof, or other substituted analogs thereof, provided that the substituent is substantially removed during drying, soaking and/or calcining and causes no adverse effects to the final catalyst and is capable of acidifying the preparation to a desired pH value, with or without the addition of a co-acidifying agent such as nitric acid. The term poly means two or more. If bismuth is used in the catalyst preparation, then the bismuth component such as bismuth nitrate or bismuth oxide is dissolved in a solution of the organic acid in the presence or absence of water, although in the presence of water is preferred. Exemplary examples of such organic acids include low to medium molecular weight linear, branched, cyclic-containing or aromatic-containing organic mono acids such as formic acid, acetic acid, propanoic acid, butanoic acid (butyric acid), isobutyric acid, pentanoic acid and its branched analogs, hexanoic acid and its branched analogs, hydroxylated analogs thereof such as ascorbic acid, higher alkanoic acids or their hydroxylated analogs or the like, or mixtures or combinations thereof and linear or branched organic diacids, triacids and polyacids such as citric acid, tartaric acid, or the like and hydroxylated analogs thereof or mixtures or combinations thereof. As used therein, the term "desired pH" means a pH that yields a catalyst composition of this invention that has a pore size distribution having at least 50% medium pores, where the exact pH will depend on the catalyst components as is well known to one of ordinary skill in the art of catalyst preparation.

Suitable ammonium-containing compounds for use in this invention include, without limitation, any ammonium compound that undergoes thermal decomposition to volatile components. Exemplary examples of such ammonium-containing compounds include, without limitation, ammonium hydroxide, ammonium nitrate, ammonium chloride, ammonium bromide, ammonium carbonate, ammonium salts of alkanoic (carboxylic) acids, or mixtures or combinations thereof. When an ammonium-containing compound is used in the catalyst preparation, a mole ratio of the molybdenum-containing compound to the ammonium-containing compound ($Mo:NH_4$) is generally between about 0.5 to about 20.0. Preferably, the mole ratio is between about 2.0 to 15.0, and, particularly, the mole ratio is between about 2.0 to about 10.0.

Under certain conditions, generally when an ammonium-containing compound is used along with the organic acid in the preparation of the catalyst of this invention, the resulting catalysts can be produced with a given pore size distribution comprising small pores, medium pores, and large pores. Small pores are pores having a diameter D less than about 100 Å, i.e., D<100 Å. Medium pores are pores having a diameter D greater than or equal to about 100 Å and less than about 1000 Å, i.e., 100 Å≦D<1000 Å. Large pores are pores having a diameter D greater than or equal to about 1000 Å, i.e., D≧1000 Å. The catalysts of this invention generally have a pore size distribution comprising between about 0.1% and about 10.0% small pores, between about 55% and about 90% medium pores and the remainder large pores. Preferably, the catalysts of this invention have a pore size distribution comprising between about 0.5% and about 7.5% of small pores, between about 55% and about 80% medium pores, and the remainder large pores. Particularly, the catalysts of this invention have a pore size distribution comprising between about 1.0% and about 5.0% small pores, at least 57% medium pores and the remainder large pores. Alternatively, the catalysts of this invention have a pore size distribution comprising at least 55% medium pores. Preferably, the catalysts of this invention have a pore size distribution comprising between about 55% medium pores and about 90% medium pores. Particularly, the catalysts of this invention have a pore size distribution comprising between about 55% medium pores and about 80% medium pores. More particularly, the catalysts of this invention have a pore size distribution comprising between about 57% medium pores and about 80% medium pores. It should be recognized by an ordinary artisan that determining or measuring the pore size or pore size distribution of the catalyst can be based on any standard method such as BET, mercury porosimeter, or similar pore size analyzer.

The present invention relates to improved catalysts for the oxidation of unsaturated and/or saturated aldehydes, where the catalysts of this invention are prepared from a precursor formulation where a bismuth component is dissolved in a solution including a sufficient amount of an organic acid to substantially dissolve the bismuth component prior to its addition to a solution containing the other components. Preferably, sufficient nitric acid is added to the resulting solution to adjust the pH to a desired pH level. Under certain conditions, the resulting catalysts can be prepared with an increased amount of medium pores, especially when an ammonium-containing compound is used in the preparation.

The catalysts of this invention are prepared using a solution of an organic acid to dissolve a bismuth component such as bismuth nitrate ($Bi(NO_3)_3$) or other bismuth salts, prior to adding the bismuth component to a solution of the other components and optionally an amount of nitric acid to adjust the pH of the resulting solution to a desired pH value. The bismuth solution is preferably substantially free of precipitates prior to being added to the solution of the other components and upon addition the bismuth solution initiates precipitation. Nitric acid referred to here means nitric acid added in producing the catalyst and excludes $NO_3$ moieties which may be part of the molecular formula for the catalytic components used in preparing the catalysts of this invention.

The catalysts of this invention are rendered more or less active by a calcination procedure to which they are subjected. The general calcination protocol is to calcine a dried catalyst at a temperature and for a time sufficient to obtain a catalyst of a desired activity, generally maximized activity. Generally, the calcination temperature is above about 350° C. and the period of time is between about 2 hours and about 24 hours; however, shorter and longer times can be used. Preferably, the calcination protocol also includes a soak step at a soak temperature and for a soak time sufficient to out gas volatile components and components that form volatile components at high temperature. The soak temperature is generally between about 180° C. and about 250° C. and the soak period of time is between about 1 hour and about 8 hours; however, shorter and longer times can be used. The soak step is designed to allow volatile components and components that form volatile components at high temperature to exit the catalyst gradually and not explosively or so rapidly that the catalyst pore distribution is damaged (collapses or produces too many large pores). In laboratory protocols, the protocols include an initial temperature ramp of about 0.25° C./min. to about 0.75° C./min. for a period of time sufficient to raise the temperature to a desired soak step temperature and a final temperature ramp of about 0.25° C./min. to about 0.75° C./min for a period of time sufficient to raise the temperature to a desired calcination step temperature. In commercial catalyst protocols, however, the ramp rates are generally much higher as is well known in the art of commercial catalyst preparation.

If an ammonium-containing compound is used in conjunction with the organic acid during catalyst preparation to control catalyst pore size distribution, then the components that produce volatile components during drying, soaking and calcining will include nitrates, ammonium salts and the organic acid or its salts. The inventors believe that although the amount of nitrate and ammonium ions present in the dried composition is important for producing the desired pore size distribution, the careful control of drying, soaking and calcining conditions is also important in controlling the number of medium pores generated in the final catalyst. If the pre-calcined catalyst is heated too fast, the volatile components have insufficient time to out-gas and the activity of the resulting catalyst is reduced. Thus, by controlling catalyst drying, soaking and calcining, component out gassing can be substantially completed before the catalyst is subjected to its final calcination temperature.

The catalyst used in the process of the present invention can be used without a carrier, or can be supported on or diluted with an inert carrier. Suitable inert carriers include, without limitation, silicates, silicas, aluminates, aluminas, silica-aluminas, silicon carbide, zirconias, titanias, magnesia, similar oxides, other heteropolyacids or mixtures or combinations thereof.

The catalysts of this invention are ideally suited for producing an unsaturated acid, preferably a conjugated unsaturated acid such as acrylic acid and/or methacrylic acid by gas-phase catalytic oxidation of a vapor or vapor stream including an unsaturated and/or saturated aldehyde, preferably, a conjugated unsaturated aldehyde such as acrolein and/or methacrolein at a temperature, at a pressure and for a time sufficient to obtain a desired conversion of the unsaturated and/or saturated aldehyde to the corresponding unsaturated acid. The vapor stream used to contact the catalysts of the present invention generally includes sufficient unsaturated conjugated aldehyde that is converted into an output stream containing commercial quantity of a corresponding unsaturated conjugated acid. For methacrolein, the vapor stream can have a wide methacrolein concentration range, preferably, the vapor or vapor stream includes from about 1 vol. % to about 20 vol. % of methacrolein, and particularly, the vapor or vapor stream includes from about 2 to about 8 vol. % of methacrolein. Typically, a methacrolein feed for the preparation of methacrylic acid may also contain large amounts of water and smaller amounts of impurities such as carbon monoxide, carbon dioxide, acetone, acetic acid, acrolein, methacrylic acid, isobutylene and other saturated and unsaturated hydrocarbons, lower saturated aldehydes, etc., but such impurities have substantially no effect on the conversion of the unsaturated and/or saturated aldehydes to unsaturated acids.

Although the gas-phase catalytic oxidation reaction of methacrolein or acrolein over a catalyst of this invention can be economically performed in the presence of air, preferably, an oxidizing agent enriched in oxygen is used. An oxygen concentration in the oxidizing gas used in the conversion of methacrolein to methacrylic acid, for example, is set relative to a molar ratio of oxygen to methacrolein. Generally, the molar ratio has a value between about 0.3 and about 4, preferably, the ratio has a value between about 0.4 and about 2.5. The oxidizing gas may be diluted with or contain an inert gas such as nitrogen, steam, carbon dioxide, etc., or mixtures or combinations thereof.

In producing methacrylic acid using the catalysts of this invention, the oxidation is generally carried out at a reaction pressure between sub-ambient and several atmospheres above ambient, preferably, the pressure is near ambient or as low as practical. The oxidation reaction using the catalysts of this invention is generally carried out at an elevated temperature, preferably, at a temperature between about 230° C. and about 450° C., particularly, at a temperature between about 250° C. and about 400° C. and more particularly, at a temperature between about 250° C. and about 350° C. The oxidation reaction using the catalysts of this invention can be carried out using a variety of reactor systems including a fixed bed reactor (a reactor having one or more fixed catalyst beds or zones), a fluidized bed reactor (recycling catalyst particles in the reactor are fluidized), a moving bed reactor (catalyst moves in and out of the catalyst zone(s)), a continuous stirred tank reactor or any other reactor system geared for carrying out an oxidizing reaction such as the conversion of unsaturated and/or saturated aldehydes to unsaturated acids.

EXPERIMENTAL SECTION

General Considerations

The following examples illustrate the preparation, calcination and testing of specific catalytic formulations of the general formula (I) and of a comparative example catalyst. Example 1 illustrates the preparation of a catalyst of this invention, while Comparative Example 1 illustrates the preparation of a comparative catalyst. Examples are also included that analyze the calcination and performance data for the catalysts of this invention and the comparative example reported herein as relative data. The activity of the comparative example catalyst was defined as 1.0, so that if a catalyst showed an activity 30% higher than the comparative example catalyst, then this catalyst would have a relative activity of 1.3. Similarly, the relative selectivity of the comparative example was defined as 0.0. The selectivity vs. conversion curve is compared between a catalyst of this invention and the comparative example catalyst, so that if the catalyst of this invention showed a selectivity 1.0% higher than comparative example catalyst at the same percentage conversion of methacrolein, then, this catalyst would have a relative selectivity of 1.0. In the following examples, when the term nitric acid is used that term means about a 70 wt. % aqueous solution of nitric acid. It should be recognized by ordinary artisans that any concentrated nitric acid solution can be used provided that the amount added is adjusted to achieve the desired mole ratio. Also in the following examples, when the term phosphoric acid is used the term means about an 85 wt. % phosphoric acid solution. It should be recognized by ordinary artisans that any concentrated phosphoric acid solution can be used provided that the amount added is adjusted to achieve the desired mole ratio. Also the term acetic acid means glacial acetic acid.

Catalysts Preparations

Example 1

The following example illustrates the preparation of a catalyst of this invention having the following formula $Mo_{12}P_{1.5}V_{0.5}Cu_{0.1}Bi_{0.5}Sb_{0.8}Cs_{1.0}B_{0.5}O_g$.

46.49 grams of ammonium paramolybdate were added to 200 mL of de-ionized (DI) water at room temperature. 1.28 grams of ammonium metavanadate were added to the above solution to produce an MoV solution. The mixture was stirred at room temperature until all particles were dissolved. 4.28 grams of cesium nitrate was then added to 25 mL of DI water, and the resulting solution was added to the MoV solution to form an MoVCs solution. 3.80 grams of phosphoric acid were then added to 6 mL of DI water and the solution obtained was added to the MoVCs solution to form an MoVCsP solution. 0.51 grams of copper nitrate were added to 5 mL of DI water and the solution obtained was added to the MoVCsP solution to form an MoVCsPCu solution. 5.32 grams of bismuth nitrate were added into an acetic acid solution including 4 mL of glacial acetic acid and 20 mL of DI water. The bismuth solution was then added to the MoVCsPCu solution forming an MoVCsPCuBi slurry. 4.30 grams of nitric acid were added to 30 mL of DI water and then added to the MoVCsPCuBi slurry to adjust a pH of the slurry to a desired pH value. The MoVCsPCuBi slurry was then heated to 95° C. and then 2.56 grams of antimony trioxide and 0.68 grams of boric acid were added to the MoVCsPCuBi slurry to form an MoVCsPCuBiSbB slurry.

The MoVCsPCuBiSbB slurry was then evaporated at between about 75 and about 100° C. to form an evaporated mixture. The evaporated mixture was then dried at about 130° C. for about 16 hours and sieved to obtain particles having a size between about 20 and 30 mesh. The particles were then heated to a soak temperature of 230° C. at a rate of 0.5° C./min and held at the soak temperature for 3 hours in air. The particles were then calcined at 370° C. at a rate of 0.5° C./min. for 5 hours in air to form the catalyst of this invention.

Example 2

The following example illustrates the preparation of a catalyst of this invention having the following formula $Mo_{12}P_{1.5}V_{0.5}Cu_{0.1}Bi_{0.5}Sb_{0.8}Cs_{1.0}B_{0.5}O_g$ by the method of Example 1, but order of addition of the bismuth solution and the nitric acid solution are reversed.

Example 3

The following example illustrates the preparation of a catalyst of this invention having the following formula $Mo_{12}P_{1.5}V_{0.5}Cu_{0.1}Bi_{0.5}Sb_{0.8}Cs_{1.0}B_{0.5}O_g$ by the method of Example 1, but 3.8 grams of nitric acid are used instead of 4.3 grams of nitric acid as in Example 1.

Example 4

The following example illustrates the preparation of a catalyst of this invention having the following formula $Mo_{12}P_{1.5}V_{0.5}Cu_{0.1}Bi_{0.3}Sb_{0.8}CS_{1.0}B_{0.5}O_g$ by the method of Example 1, but the amount of bismuth nitrate used yielded a final Bi mole amount of 0.3 instead of 0.5 as in Example 1.

Example 5

The following example illustrates the preparation of a catalyst of this invention having the following formula $Mo_{12}P_{1.5}V_{0.5}Cu_{0.2}Bi_{0.5}Sb_{0.8}CS_{1.0}B_{0.5}O_g$ by the method of Example 1, but the amount of copper nitrate used yielded a final Cu mole amount of 0.2 instead of 0.1 as in Example 1 and the amount of glacial acetic acid used was 2.0 mL instead of 4.0 mL as in Example 1 and the amount of nitric acid used was 3.8 grams instead of 4.3 grams as in Example 1.

Example 6

The following example illustrates the preparation of a catalyst of this invention having the following formula $Mo_{12}P_{1.5}V_{0.5}Cu_{0.1}Bi_{0.5}Sb_{0.8}Cs_{1.0}B_{0.5}O_g$ by the method of Example 1, but the amount of glacial acetic acid used was 2.0 mL instead of 4.0 mL as in Example 1 and the amount of nitric acid used was 3.8 grams instead of 4.3 grams as in Example 1.

Example 7

The following example illustrates the preparation of a catalyst of this invention having the following formula $Mo_{12}P_{1.5}V_{0.5}Cu_{0.1}Bi_{0.5}Sb_{0.5}Cs_{1.0}B_{0.5}O_g$ by the method of Example 1, but the amount of antimony oxide used yielded a final Sb mole amount of 0.5 instead of 0.8 as in Example 1 and the amount of nitric acid used was 3.8 grams instead of 4.30 grams as in Example 1.

Example 8

The following example illustrates the preparation of a catalyst of this invention having the following formula $Mo_{1.2}P_{15}V_{0.5}Cu_{0.1}Bi_{0.5}Sb_{0.8}Cs_{1.0}B_{0.5}O_g$, where no nitric acid is used to adjust the pH.

46.49 grams of ammonium paramolybdate were added to 200 mL of de-ionized (DI) water at room temperature. 1.28 grams of ammonium metavanadate were added to the above solution to produce an MoV solution. The mixture was stirred at room temperature until all particles were dissolved. 4.28 grams of cesium nitrate was then added to 25 mL of DI water, and the resulting solution was added to the MoV solution to form an MoVCs solution. 3.80 grams of phosphoric acid were then added to 6 mL of DI water and the solution obtained was added to the MoVCs solution to form an MoVCsP solution. 0.51 grams of copper nitrate were added to 5 mL of DI water and the solution obtained was added to the MoVCsP solution to form an MoVCsPCu solution. 5.32 grams of bismuth nitrate were added into an acetic acid solution including 4 mL of glacial acetic acid and 8 mL of DI water and after bismuth nitrate dissolution, 12 additional mL of DI water were added to the acetic acid solution. The bismuth solution was then added to the MoVCsPCu solution forming an MoVCsPCuBi slurry. The MoVCsPCuBi slurry was then heated to 95° C. and then 2.56 grams of antimony trioxide and 0.68 grams of boric acid were added to the MoVCsPCuBi slurry to form an MoVCsPCuBiSbB slurry.

The MoVCsPCuBiSbB slurry was then evaporated at between about 75° C. and about 100° C. to form an evaporated mixture. The evaporated mixture was then dried at about 130° C. for about 16 hours and sieved to obtain particles having a size between about 20 and 30 mesh. The particles were then heated to a soak temperature of 230° C. at a rate of 0.5° C./min and held at the soak temperature for 3 hours in air. The particles were then heated to a calcination temperature of 370° C. at a rate of 0.5° C./min. for 5 hours in air to form the catalyst of this invention.

Example 9

The following example illustrates the preparation of a catalyst of this invention having the following formula $Mo_{12}P_{1.5}V_{0.5}Cu_{0.1}Bi_{0.5}Sb_{0.8}Cs_{1.0}B_{0.5}O_g$ by the method of Example 9, but 10 mL of acetic acid instead of 4 mL as in Example 8.

Example 10

The following example illustrates the preparation of a catalyst of this invention having the following formula $Mo_{12}P_{1.5}V_{0.5}Cu_{0.1}Bi_{0.5}Sb_{0.8}Cs_{1.0}B_{0.5}O_g$ by the method of Example 8, but 20 mL of acetic acid instead of 4 mL as in Example 8.

Comparative Example 1

The following comparative example illustrates the preparation of a comparative catalyst for purposes of comparing the catalyst of Example 1, where the comparative catalyst has a formula $MO_{12}P_{1.5}V_{0.5}CU_{0.1}Bi_{0.5}Sb_{0.8}CS_{1.0}B_{0.5}O_g$ identical to that of the catalyst of Example 1, with the exception that the catalyst preparation includes nitric acid instead of acetic acid to dissolve the bismuth component for the purpose of comparing a catalyst prepared with an organic acid to the catalysts of this invention.

46.50 grams of ammonium paramolybdate were added to 200 mL of de-ionized (DI) water at room temperature. 1.28 grams of ammonium metavanadate were added to the above solution to produce a MoV solution. The mixture was stirred at room temperature until all particles were dissolved. 4.28 grams of cesium nitrate was then added to 25 mL of DI water, and the resulting solution was added to the MoV solution to form a MoVCs solution. 3.80 grams of phosphoric acid were then dissolved in 6 mL of DI water and the solution obtained was added to the MoVCs solution to form a MoVCsP solution. 0.51 grams of copper nitrate were added to 5 mL of DI water and the solution obtained was added to the MoVCsP solution to form a MoVCsPCu solution. 4.30 grams of nitric acid were added to 30 mL of DI water, then 5.32 grams of bismuth nitrate were added to the nitric acid solution and the mixture was stirred until the bismuth nitrate went into solution. The bismuth solution was then added to the MoVCsPCu solution forming a MoVCsPCuBi slurry. The MoVCsPCuBi slurry was then heated to 95° C. and then 2.56 grams of antimony trioxide and 0.68 grams of boric acid were added to the MoVCsPCuBi slurry to form a MoVCsPCuBiSbB slurry.

The MoVCsPCuBiSbB slurry was then evaporated at between about 75° C. and about 100° C. to form a evaporated mixture. The evaporated mixture was then dried at about 130° C. for about 16 hours and sieved to obtain particles having a size between about 20 and 30 mesh. The particles were then heated to a soak temperature of 230° C. at a rate of 0.5° C./min and held at the soak temperature for 3 hours in air. The particles were then heated to a calcination temperature of 370° C. at a rate of 0.5° C./min. for 5 hours in air to form Comparative Example 1.

Catalyst Testing and Performance Data 6 cc of either the Example 1 or the Comparative Example 1 catalyst were diluted with 9 cc of quartz chips and were loaded into a fixed bed reactor. The catalysts were tested with a vapor stream having the following composition: 4 vol. % methacrolein, 8 vol. % oxygen, and 30 vol. % steam with the balance being nitrogen. By varying reaction temperature and vapor stream flow rate, conversion and selectivity data were obtained under a variety of conditions. The resulting effluent stream was analyzed by gas chromatography.

To understand the following results, the following definitions are set forth:

% conversion={[moles of MAC converted)]/[(moles of unconverted MAC−moles of MAC converted]}*100

% selectivity={[(moles of MAA produced)]/[(moles of all products produced)]}*100 where MAA is methacrylic acid, MAC is methacrolein and the moles of all products produced is on a four-carbon product count.

The Comparative Example 1 catalyst was tested under three conditions of flow rate in sccm at three different temperatures. The resulting data is tabulated in Table I.

TABLE I

Catalytic Performance of Comparative Example 1 Catalyst

| Flowrate (sccm) | Temperature (° C.) | Conversion (%) | Selectivity (%) |
| --- | --- | --- | --- |
| 100 | 290 | 61.3 | 87.0 |
| 57 | 299 | 88.6 | 83.5 |
| 50 | 298 | 93.9 | 82.1 |

The Example 1-7 catalysts were tested under identical flow rate and reaction temperature conditions. The resulting data is tabulated in Table II.

TABLE II

Catalytic Performance of Examples 1-7 Catalysts

| Catalyst | Relative Activity | Relative Selectivity |
| --- | --- | --- |
| Comparative Example 1 | 1.0 | 0.0 |
| Example 1 | 0.9 | 0.5 |
| Example 2 | 1.0 | 0.0 |
| Example 3 | 1.5 | 0.5 |

TABLE II-continued

Catalytic Performance of Examples 1-7 Catalysts

| Catalyst | Relative Activity | Relative Selectivity |
| --- | --- | --- |
| Example 4 | 1.3 | 2.0 |
| Example 5 | 1.8 | −0.5 |
| Example 6 | 1.5 | 0.5 |
| Example 7 | 1.8 | 0.0 |

The error in the relative activity data is about ±10% and the error in relative selectivity is about ±1%.

The results of Table II clearly show that variations in the catalyst preparation procedure do cause changes to the catalysts' relative activity and selectivity, but that the catalysts all fall into a range between about 1.0 and about 2.0 for relative activity and a range between about −0.5 and about 2.0 for relative selectivity.

The Example 8-10 catalysts were tested under identical flow rate and reaction temperature conditions. The resulting data is tabulated in Table III.

TABLE III

Catalytic Performance of Examples 8-10 Catalysts

| Catalyst | Relative Activity | Relative Selectivity |
| --- | --- | --- |
| Example 8 | 1.3 | 0.0 |
| Example 9 | 1.9 | 0.0 |
| Example 10 | 2.8 | 0.0 |

The error in the relative activity data is about ±10% and the error in relative selectivity is about ±1%.

The results of Table III clearly shows that variations in the catalyst preparation procedure where no nitric acid is used yielded catalysts with improved relative activity, while maintaining relative selectivity.

Thus, catalysts made using glacial acetic acid with or without the use of nitric acid to adjust solution pH have a relative activity between about 1.0 and about 3.0 and a relative selectivity between about −0.5 and about 2.0.

All references cited herein are incorporated by reference. While this invention has been described fully and completely, it should be understood that, within the scope of the appended claims, the invention may be practiced otherwise than as specifically described. Although the invention has been disclosed with reference to its preferred embodiments, from reading this description those of skill in the art may appreciate changes and modification that may be made which do not depart from the scope and spirit of the invention as described above and claimed hereafter.

We claim:

1. method for preparing an heteropolyacid catalyst for converting unsaturated and/or saturated aldehydes to unsaturated acids comprising the steps of:
   mixing together a pre-catalyst composition and an acid composition,
      where the pre-catalyst composition comprises:
         molybdenum and phosphorus in a 12:a mole ratio, and
      where the acid composition comprises:
         an amount of an organic acid, precipitating the acidified pre-catalyst composition to form a pre-catalyst, drying the pre-catalyst to form a dried pre-catalyst, and
   calcining the dried pre-catalyst to form an heteropolyacid catalyst,
   where a is a number having a value between about 0.5 and about 3.5 and the amount of the organic acid in the acid composition is sufficient to acidify the pre-catalyst composition to a desired pH value.

2. The method of claim 1, wherein the pre-catalyst composition further comprises:
vanadium (V) in a 12:a:b mole ratio,
where b is a number having a value between about 0.01 and about 5.0.

3. The method of claim 1, wherein the pre-catalyst composition and/or the acid composition further comprise:
copper (Cu) in a 12:a:c mole ratio,
where c is a number having a value between 0.0 and about 1.5.

4. The method of claim 1, wherein the pre-catalyst composition, the acid composition the pre-catalyst, and/or the dried pre-catalyst further comprise:
a component selected from the group consisting of potassium (K), rubidium
(Rb), cesium (Cs), thallium (T1), and mixtures or combinations thereof in a
12:a:e mole ratio,
where e is a number having a value between about 0.2 and about 2.5.

5. The method of claim 1, wherein the pre-catalyst composition, the acid composition, the pre-catalyst, and/or the dried pre-catalyst further comprise:
a component selected from the group consisting of antimony (Sb), boron (B), tungsten (W), cerium (Ce), niobium (Nb), indium (In), iron (Fe), chromium (Cr), cobalt (Co), nickel (Ni), manganese (Mn), arsenic (As), silver (Ag), zinc (Zn), lead (Pb), tin (Sn), titanium (Ti), aluminum (Al), silicon (Si), tantalum (Ta), germanium (Ge), gallium (Ga), zirconium (Zr), magnesium (Mg), barium (Ba), lanthanum (La), and mixtures or combinations thereof in a 12:a:f mole ratio,
where f is a number having a value between 0.0 and about 5.0.

6. The method of claim 1, wherein the pre-catalyst composition and/or the acid composition further comprises:
an effective amount of an ammonium-containing component, where the effective amount is sufficient to produce a pore size distribution comprising at least 57% medium pores in the catalyst.

7. The method of claim 6, wherein the amount of the organic acid and the effective amount of the ammonium-containing compound produce the pore size distribution.

8. The method of claim 1, wherein the acid composition further comprises:
bismuth (Bi) in a 12:a:d mole ratio,
vanadium (V) in a 12:a:b:d mole ratio,
copper (Cu) in a 12:a:b:c:d mole ratio,
a first component selected from the group consisting of potassium (K),
rubidium (Rb), cesium (Cs), thallium (T1), and mixtures or combinations thereof in a 12:a:b:c:d:e mole ratio,
a second component selected from the group consisting of antimony (Sb), boron (B), tungsten (W), cerium (Ce), niobium (Nb), indium (In), iron (Fe), chromium (Cr), cobalt (Co), nickel (Ni), manganese (Mn), arsenic (As), silver (Ag), zinc (Zn), lead (Pb), tin (Sn), titanium (Ti), aluminum (Al), silicon (Si), tantalum (Ta), germanium (Ge), gallium (Ga), zirconium (Zr), magnesium (Mg), barium (Ba), lanthanum (La), and mixtures or combinations thereof in a 12:a:b:c:d:e:f mole ratio,
where b is a number having a value between about 0.01 and about 5.0,
where c is a number having a value between about 0.01 and about 1.5;
where d is a number having a value between about 0.01 and about 2.0,
where e is a number having a value between about 0.01 and about 2.5, and
where f is a number having a value between about 0.01 and about 5.0.

9. The method of claim 1, wherein the pre-catalyst composition and the acid composition are solutions substantially free of precipitates.

10. The method of claim 1, further comprising the step of:
soaking the dried pre-catalyst according to a soak protocol, where the protocol is sufficient to allow volatile compounds or compounds that produce volatile compounds upon heating to escape the dried catalyst in a controlled manner.

11. A method for preparing an heteropolyacid catalyst for converting unsaturated and/or saturated aldehydes to unsaturated acids comprising the steps of:
mixing a first solution and a second solution to form a slurry,
where the first solution comprises:
molybdenum and phosphorus in a 12:a mole ratio, and
where the second solution comprises:
bismuth (Bi) in a 12:a:d mole ratio and an amount of an organic acid,
drying the slurry to form a dried pre-catalyst, and
calcining the dried pre-catalyst to form an heteropolyacid catalyst,
where a is a number having a value between about 0.5 and about 3.5, d is a number having a value between about 0.01 and about 2.0, and the amount of the organic acid is sufficient to completely dissolve the d moles of bismuth.

12. The method of claim 11, wherein the first solution further comprises:
vanadium (V) in a 12:a:b:d mole ratio,
where b is a number having a value between about 0.01 and about 5.0.

13. The method of claim 11, wherein the first solution and/or the second solution further comprise:
copper (Cu) in a 12:a:b:c:d mole ratio,
where c is a number having a value between 0.0 and about 1.5.

14. The method of claim 11, wherein the first solution, the second solution, the slurry, and/or dried pre-catalyst further comprise:
a first component selected from the group consisting of potassium (K), rubidium (Rb), cesium (Cs), thallium (Tl), and mixtures or combinations thereof in a 12:a:b:c:d:e mole ratio,
where e is a number having a value between about 0.2 and about 2.5.

15. The method of claim 14, wherein the the first solution, the second solution, the slurry, and/or dried pre-catalyst further comprise:
a second component selected from the group consisting of antimony (Sb), boron (B), tungsten (W), cerium (Ce), niobium (Nb), indium (In), iron (Fe), chromium (Cr), cobalt (Co), nickel (Ni), manganese (Mn), arsenic (As), silver (Ag), zinc (Zn), lead (Pb), tin (Sn), titanium (Ti), aluminum (Al), silicon (Si), tantalum (Ta), germanium (Ge), gallium (Ga), zirconium (Zr), magnesium (Mg), barium (Ba), lanthanum (La), and mixtures or combinations thereof in a 12:a:b:c:d:e:f mole ratio,
where f is a number having a value between 0.0 and about 5.0.

16. The method of claim 11, wherein the pre-catalyst composition and/or the acid composition further comprises:

an effective amount of an ammonium-containing component, where the effective amount is sufficient to produce a pore size distribution comprising at least 57% medium pores in the catalyst.

17. The method of claim 16, wherein the amount of the organic acid and the effective amount of the ammonium-containing compound produce the pore size distribution.

18. The method of claim 11, wherein the pre-catalyst composition and the acid composition are solutions substantially free of precipitates.

19. The method of claim 11, further comprising the step of:

soaking the dried pre-catalyst according to a soak protocol, where the protocol is sufficient to allow volatile compounds or compounds that produce volatile compounds upon heating to escape the dried catalyst in a controlled manner.

\* \* \* \* \*